United States Patent [19]
Staab et al.

[11] 3,932,041
[45] Jan. 13, 1976

[54] CONSTRUCTION UNIT FOR TWO BEAM PHOTOMETERS

[75] Inventors: Joachim Staab; Willy Apel, both of Frankfurt am Main; Achim Dräger, Eschhorn; Wilhelm-Rüdiger Haberditz, Steinbach/Ts.; Walter Fabinksi, Hattersheim, all of Germany

[73] Assignee: Hartmann & Braun Aktiengesellschaft, Frankfurt, Germany

[22] Filed: Jan. 6, 1975

[21] Appl. No.: 538,768

[30] Foreign Application Priority Data
Jan. 16, 1974 Germany............................ 7401319

[52] U.S. Cl. .............. 356/229; 250/233; 350/274; 356/204
[51] Int. Cl.² ............................................. G01J 1/10
[58] Field of Search ..... 250/233; 350/274; 356/188, 356/204, 229, 217

[56] References Cited
UNITED STATES PATENTS
| | | |
|---|---|---|
| 2,227,147 | 12/1940 | Lindsay............................ 250/233 |
| 3,709,600 | 1/1973 | Ganshorn........................... 250/233 |
| 3,715,153 | 2/1973 | Schunck et al. ..................... 250/233 |

FOREIGN PATENTS OR APPLICATIONS
| | | |
|---|---|---|
| 1,389,955 | 1/1965 | France............................... 356/217 |

*Primary Examiner*—Alfred E. Smith
*Assistant Examiner*—Richard A. Rosenberger
*Attorney, Agent, or Firm*—Ralf H. Siegemund

[57] ABSTRACT

A cylindrical block is provided with two ducts, forming a V whose legs terminate in exit windows in one axial end face of the block. A light source is disposed in the bottom of the V to direct light into both ducts. The block is further traversed by a bore, terminating as to one end in between the windows, avoiding the ducts and terminating in an offset position relative to the V-bottom and the light source at the other end of the block. A shaft traverses this bore for rotating a shutter in front of the windows. A complementary, light receiving unit is disposed with misaligned entrance windows in front of the unit windows, but their centers are traversed respectively by the optical axes of the ducts.

8 Claims, 2 Drawing Figures

U.S. Patent   Jan. 13, 1976   3,932,041
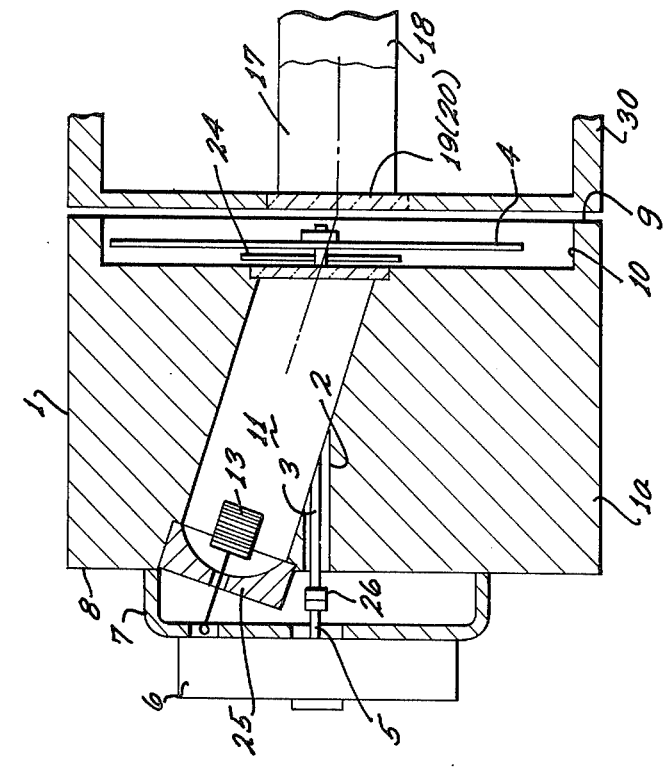
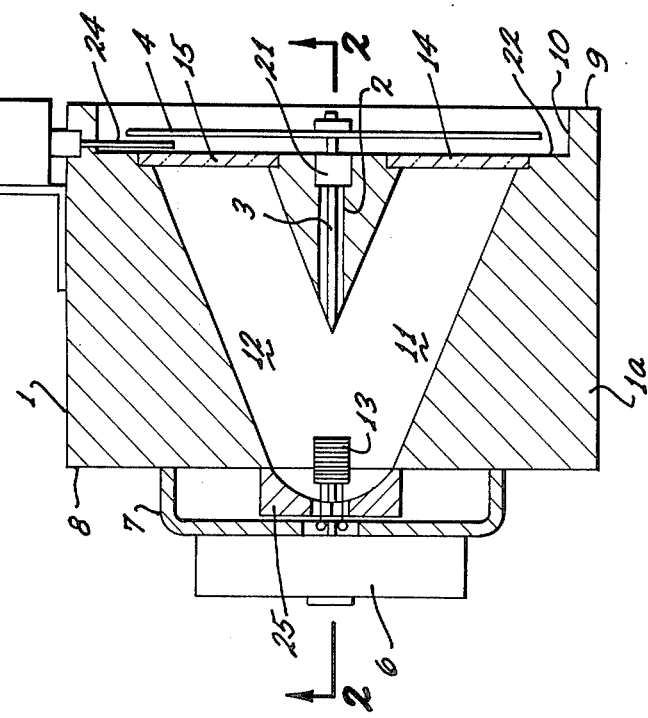

3,932,041

CONSTRUCTION UNIT FOR TWO BEAM PHOTOMETERS

BACKGROUND OF THE INVENTION

The present invention relates to two beam photometers and more particularly to improvements in the construction of such photometers.

Two beam photometers include, for example, a single light source and means to establish two beams, one to serve as measuring beam, the other one as reference beam. Light source and beam paths are, for example, included in a block with V-shaped ducts of equal lengths, wherein the bottom of the V defines the location of the source, and the duct ends (ends of the legs of the V) are closed physically by means of windows. Moreover, a rotating shutter diaphragm is disposed in the block for rotation so as to intercept both beams. The shutter disk or diaphragm is seated on a shaft which traverses the block and extends from a motor which, in turn, is affixed to the block.

German printed patent application 2,052,609, and corresponding U.S. Pat. No. 3,715,153, issued to Schunck et al, describes a particularly shaped rotating shutter with excentric disposition in relation to the exit windows of such a block.

DESCRIPTION OF THE INVENTION

It is an object of the present invention to improve on the block construction for such photometers under utilization of rather simple rotating shutters being, for example, of symmetrical wing construction.

In accordance with the preferred embodiment of the invention, it is suggested to provide a block with an optical exit plane for two side by side positioned, coplanar windows. A straight bore for the shutter shaft traverses the block in a mid-vertical line between and normal to these windows. The block includes light ducts extending in V-shaped configuration and orientation from the source of radiation, but avoids the bore due to oblique position of the ducts. Specifically, these ducts are inclined to said window plane and in both, a first plane of symmetry that includes said line and bore, and a second plane transversely to said first plane but also including said line and bore, so that neither duct is passed through by said bore, and the source of light is located in offset position relative to the motor shaft traversing the bore.

In the preferred form, the block should be of cylindrical construction and the windows are located in one axial end face of the cylinder. The shaft and bore run parallel to, but do not coincide with the axis of that cylinder. It can be assumed that a cylindrical unit is connected to that end face and which includes test fluid and reference chambers. The optical center axes of the ducts should intercept the centers of the entrance windows of that second cylinder unit.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 is a cross-section through a light source and duct block for a photometer in accordance with the preferred embodiment of the present invention; and FIG. 2 is a cross-section along line 2—2 in FIG. 1, but showing in addition attachment to a unit with test fluid and reference chambers.

Proceeding now to the detailed description of the drawings, the Figures show a metal block 1 of cylindrical configuration; reference numeral 1a in particular denotes the cylindrical surface. The cylindrical block has a first axial end face 8 and a second axial end face 9. However, a large recess 10 is formed in the latter end of the cylindrical block, and the flat bottom 22 thereof could be construed as end face of the cylindrical block, with an axial rim extending beyond bottom-end face 22.

The block is traversed by a bore 2 running parallel to but not in the center axis of the cylinder (see FIG. 2). Bore 2 is traversed by a shaft 3, which is connected to a shaft 5, extending from a motor 6. The two shafts 3 and 5 are interconnected by means of an elastic coupling. The motor is mounted to cylinder face 8 by means of a spacer and support element 7.

A rotating, wing-type shutter 4 is mounted to shaft 3 for rotation in recess 10 of the cylindrical block. Shaft 3 is mounted in a bearing block 21, which slides in a groove transverse to the plane of FIG. 1 and right at the location, where the bore 2 terminates in the bottom 22 of recess 10. The shutter 4 revolves adjacent to that bottom 22.

A reflector 25 is mounted obliquely to surface 8, adjacent to motor 6, but offset from the shafts 3, 5. A filament 13 is disposed in relation to the reflector, so that a divergent light beam is formed by the reflector and directed into two ducts 11 and 12, forming a V.

The two ducts end in the plane of the bottom 25 of recess 10 and are covered by window panes 14 and 15. The shutter disk 4 rotates in front of the two windows 14, 15, whereby interception may occur simultaneously or in phase opposition.

One can see from the drawings that the two ducts 11 and 12 are inclined in both planes of the drawings, so that both of them are offset and do not traverse or intercept but avoid bore 2. One can also say that the plane of the V is inclined by less than 90° to the plane of the two windows, so that the two ducts do not interfere with the shaft bore, even though the shaft bore terminates in bottom 22 centrally between the two windows 14, 15.

FIG. 2 shows also parts of a second cylindrical unit 30, having the same cylindrical diameter as block 1. Unit 30 has two tubes 17 and 18 which are misaligned in relation to the two windows 15 and 14, particularly with regard to axial light entrance windows 19 and 20. The misalignment is chosen to that upon mounting or otherwise positioning units 30 and 1 in mutual axial end face abutting disposition; the optical axes of the ducts 11, 12 as extended out of the windows 14, 15 will traverse the mid points of the two windows 19, 20.

As stated, shaft 3 is journalled in a little bearing block 21 which is slidably positioned in a groove in the bottom 22. The groove runs transversely to the plane of the drawing of FIG. 1. The adjustment range, of course, does not exceed the lateral play of shaft 3 in bore 3. The position of block 21 may be adjusted in any suitable manner, but once adjusted, the block 21 is clamped into position. This particular possibility for adjusting the shaft 3 is advantageous when motor shaft (5) and shutter shaft (3) are interconnected by an elastic coupling, such as 26. This facilitates start up, because one usually employs synchronous miniature motors, which produce a very small torque only. No large torque is needed, because once started, there is very little load on the motor. The shutter 4 can be of rather light construction. Adjusting the position of shaft 3 actually amounts to adjustment of the shutter phase. Small tilting of that shaft has no detrimental consequences.

Finally, it should be mentioned that an adjusting motor or solenoid 23 is laterally affixed to cylindrical block 1. The device 23 adjusts disposition of a light stop diaphragm 24 reaching into the light path from window 15. This diaphragm 24 shades a small portion of window 15. Such shading and light stop function is needed to balance the luminous outputs of the two ducts, to obtain optical symmetry in the two light paths before reaching the two tubes 18, 19. The diaphragm 24 is introduced inside of recess 10 between window 15 and shutter 4.

The invention is not limited to the embodiments described above, but all changes and modifications thereof not constituting departures from the spirit and scope of the invention are intended to be included.

We claim:

1. Unit for two beam photometers using a block, there being a bore traversing the block from one end to the other; shaft means traversing said bore; a motor mounted to said block and connected to said shaft means; a shutter connected to said shaft means, the improvement comprising:

a pair of ducts in the block arranged in V-shaped configuration and having one end each terminating in two windows arranged symmetrically to termination of the bore at the one end of the block, the shutter rotating in front of said windows; and the ducts of the V being inclined to avoid said bore, the duct ends at the bottom of the V being offset from the bore at the other block end, there being a source for radiation disposed in the bottom end of the V as formed by the ducts.

2. Unit as in claim 1, the windows being co-planar, the ducts each being inclined in a first plane of symmetry between the windows and including said bore, as well as in a second plane transversely thereto, and also including said bore.

3. Unit as in claim 2, the block being cylindrical, the windows being in one axial end face of the block.

4. Unit as in claim 3, the one end having a recess, the shutter running in said recess.

5. Unit as in claim 2, the shaft means being mounted for slight lateral displacement transverse to a connecting line between the centers of the windows.

6. Unit as in claim 1 and including a light stopping diaphragm adjustibly disposed in front of one of said windows.

7. Unit as in claim 1 and including a second unit disposed adjacent said windows and having a pair of entrance windows being misaligned respectively with said windows of the block, so that the center axes of the ducts respectively traverse the midpoints of said entrance windows.

8. Unit as in claim 1, the shaft means including elastically interconnected shafts, one thereof holding the shutter, the other one being a driven shaft, the shutter end of the one shaft being mounted for lateral displacement.

* * * * *